US00PP10233P

United States Patent [19]

Fear et al.

[11] Patent Number: Plant 10,233

[45] Date of Patent: Feb. 10, 1998

[54] APRICOT TREE CV. 'SUAPRISIX'

[75] Inventors: Carlos D. Fear, Aptos; Bruce D. Mowrey, La Selva Beach; David W. Cain, Bakersfield, all of Calif.

[73] Assignee: Sun World, Inc., Bakersfield, Calif.

[21] Appl. No.: 694,187

[22] Filed: Aug. 8, 1996

[51] Int. Cl.[6] ..... A01H 5/00

[52] U.S. Cl. ..... Plt./39

[58] Field of Search ..... Plt./39

*Primary Examiner*—James R. Feyrer

*Attorney, Agent, or Firm*—Knobbe, Martens, Olson & Bear, LLP

[57] ABSTRACT

A new and distinct apricot tree variety characterized by the early ripening of its fruit which exhibits an intense red external blush and has a strong apricot flavor.

1 Drawing Sheet

BACKGROUND AND SUMMARY OF THE INVENTION

This invention relates to the discovery and asexual propagation of a new variety of hybrid apricot tree, *Prunus armeniaca* cv. 'Suaprisix'. The variety is an an early ripening apricot, having attractive color and strong apricot flavor, and cultivated for the fresh fruit market. It was discovered on May 9, 1990 in Wasco, Kern County, Calif., the new variety being hybridized by Carlos D. Fear, and selected and evaluated by Bruce D. Mowrey and David W. Cain.

The variety has as its seed parent, Apricot tree cv. 'Suapritwo' (U.S. Plant Pat. No. 7,550), and its pollen parent is an unnamed, unpatented apricot tree selection identified in the breeders' plant collection as selection 427-224, which was an open pollinated seedling of the Annabelle variety. The parent varieties were first crossed in February 1987, and the resulting seed was harvested and sowed in September 1987, with the date of first flowering being February 1990. The new 'Suaprisix' variety was first propagated by Bruce D. Mowrey in June 1990, at a ranch near Wasco, Kern County, Calif., by budding onto Nemared rootstock.

The new variety cv. 'Suaprisix' may be distinguished from other presently available commercial apricot tree cultivars by the following combination of characteristics: the fruit of the new 'Suaprisix' apricot variety ripens earlier than other commonly grown varieties in the San Joaquin Valley; it ripens about 4 to 5 days ahead of the Castlebrite variety (an unpatented variety) and, thus, is usually eating ripe in Wasco, Calif. about May 10; it can be distinguished from Castlebrite by its much more intense red external blush and markedly better eating quality; it has a higher sugar-to-acid ratio than Castlebrite and has a much stronger and more pronounced apricot flavor compared to Castlebrite; and the variety is more regular in bearing than Castlebrite and produces more abundant crops in years having a low accumulation of winter chilling hours (hours of temperatures between 32° F.and 45° F.).

The new variety may be distinguished from its pollen parent, selection 427-224, by the following combination of characteristics: the fruit of 'Suaprisix' ripens 5 days earlier; it has better external color; and its has a smoother, more rounded shape than selection 427-224. The new variety may be distinguished from its seed parent, 'Suapritwo', by the following combination of characteristics: the 'Suaprisix' fruit resembles that of its seed parent in possessing higher and more attractive external red blush than most apricot varieties and having a strong apricot flavor with a good sugar-to-acid ratio; it differs from the fruit of its seed parent by ripening about 10 days earlier and having smaller fruit size; the new variety is pollen fertile while 'Suapritwo' is pollen sterile; and it bears better crops than its seed parent during years having a low accumulation of winter chilling hours. The new 'Suaprisix' variety has been shown to maintain the distinguishing characteristics through successive asexual propagations by, for example, budding.

BRIEF DESCRIPTION OF THE FIGURE

The accompanying drawing in FIG. 1 illustrates, in full color, a typical stem and mature leaves of the new apricot tree variety, and the outer surface of ripe fruit as viewed perpendicular to the suture line plane and looking at the suture line. The drawing also illustrates the fruit of the new variety sectioned in half from end to end, with the stone removed from the flesh.

DETAILED BOTANICAL DESCRIPTION OF THE INVENTION

Figure 1:
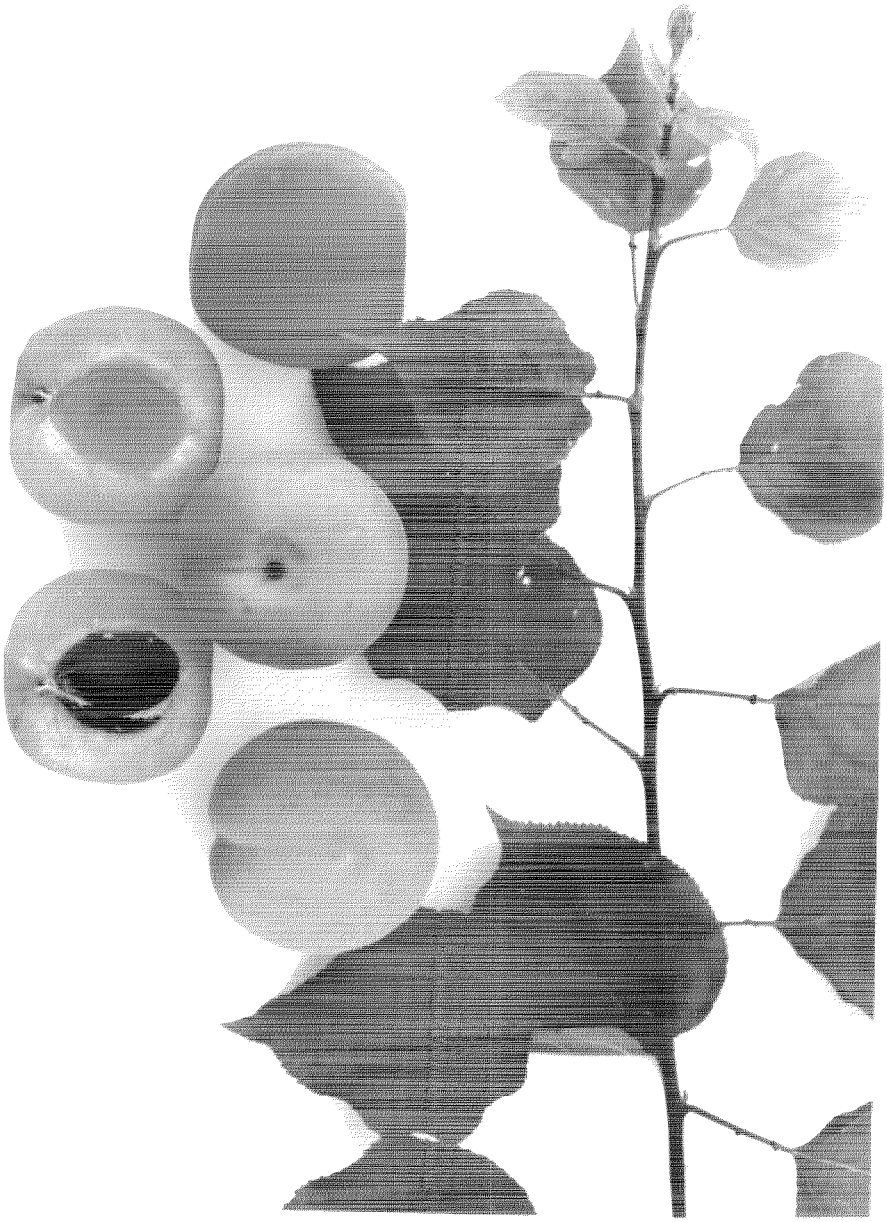

Throughout this specification, color names beginning with a small letter signify that the name of that color, as used in common speech, is aptly descriptive. Color names beginning with a capital letter designate values based upon R.H.S. Colour Chart, published by The Royal Horticultural Society, London, England.

The descriptive matter which follows pertains to 'Suaprisix' plants grown in the vicinity of Wasco, Kern County, Calif. during 1994, and is believed to apply to plants of the variety grown under similar conditions of soil and climate elsewhere:

TREE

General:

*Size.*—Medium.
*Vigor.*—Medium.
*Habit.*—Semi-upright.
*Density of foliage.*—Medium.
*Shape.*—Round.
*Hardiness.*—Hardy, in Wasco, Calif.
*Productivity.*—Medium productive.
*Fruit bearing.*—Regular bearer.
*Root stock.*—Nemared.

Trunk:

*Shape.*—Medium.
*Surface texture.*—Medium.

Branches:

*Shape.*—Medium.

*Surface texture.*—Medium.
*Surface appearance.*—Semi-glossy.
Lenticels:
*Number.*—Medium.
*Size.*—Medium.

LEAVES

General:
*Average length.*—About 12 cm.
*Average width.*—About 6.5 cm.
*Size.*—Medium.
*Outline.*—Spatulate.
*Profile.*—Up folded.
*Leaf blade tip.*—in the plane of the leaf.
*Angle of tip.*—Acute.
*Margin.*—Serrate.
*Undulation of margin.*—Slight.
*Apex.*—Acuminate.
*Base.*—U-shaped.
*Thickness.*—Medium.
Upper surface;
*Color.*—Green 137B.
*Glossiness.*—Weak.
*Pubescence.*—Absent.
*Surface texture.*—Smooth.
*Surface appearance.*—Dull.
Lower surface:
*Color.*—Green 137C.
*Glossiness.*—Weak.
*Pubescence.*—Absent.
*Surface texture.*—Smooth.
*Surface appearance.*—Dull.
Petiole:
*Length.*—Long.
*Thickness.*—Slender.
Glands:
*Average number.*—2.
*Positioning.*—(a) On petiole. (b) Alternate.
*Size.*—Small
*Shape.*—Globose.
*Color.*—Brown 200C.
Stipules:
*Persistence.*—Fall off.
Wood (leaf) buds:
*Shape.*—Rounded.
*Size.*—Small.
*Position relative to shoot.*—Held out.
*Support.*—Not decurrent.
*Size.*—Medium.
*Time of bud burst.*—*Early.*

FLOWERING SHOOTS

Anthocyanin coloration:
*Presence.*—Present.
*Intensity.*—Medium.
Thickness: Thick; about 1.5 cm.
Internode length: Medium; about 1.3 cm.
Buds:
*Density.*—Medium.
*Distribution.*—On spurs and one year old shoots.
*Ratio of wood (leaf) buds to flowering shoots.*—1:2.

FLOWERS

General:
*Date of first bloom.*—Feb. 26, 1994.
*Date of full bloom.*—Mar. 3, 1994.
*Time of bloom.*—Average, as compared with similar varieties in the growing area of Wasco, Calif.
*Duration of bloom.*—Average.
*Size (fully opened flower).*—Medium; about 3.0 cm (diameter).
*Shape.*—Rosaceous.
*Petals.*—Overlapping.
*Color (fully opened flower).*—White 155D.
Flower-Buds:
*Hardiness.*—Hardy, in Wasco, Calif.
*Size.*—Medium.
*Length.*—Medium.
*Shape.*—Pointed; plump.
*Positioning.*—Free.
*Pubescence.*—Absent.
*Color.*—Greyed-Orange 166B.
Peduncle:
*Length.*—Short.
*Thickness.*—Medium.
*Pubescence.*—Few.
Receptacle:
*Depth.*—Medium.
*Pubescence of inner surface (at white bud stage).*—Absent.
*Pubescence of outer surface.*—Few.
Sepals:
*Positioning.*—Touching receptacle.
*Shape.*—Triangular.
*Pubescence of inner surface.*—Absent.
*Pubescence of outer surface.*—Few.
*Frequency of double sepals.*—Few; frequently have 6 sepals.
Petals:
*Frequency of double petals.*—Few: frequently have 6 sepals.
*Size.*—Medium; about 1.3 cm. in width.
*Shape.*—Circular.
*Claw length.*—Short.
*Margin waviness.*—Weak to absent.
*Base angle.*—Wide.
*Division of upper margin.*—Entire.
*Pubescence of inner surface.*—Absent.
*Pubescence of outer surface.*—Absent.
*Color.*—Inner surface: White 155D. Outer surface: White 155D.
Stigma:
*Position (as compared with anthers).*—Slightly above.
Anthers:
*Color (just before dehiscence).*—Yellow-Orange 17B.
Pollen:
*Color.*—Yellow 13B.
Stamens:
*Position.*—Perigynous.
Pistil:
*Frequency of supplementary.*—Few.
*Number.*—Sometimes more than one.
Ovary:
*Pubescence.*—Pubescent; medium.
*Density of hairs.*—Medium to slight.
Style:
*Pubescence (of base).*—Medium.
*Density of hairs.*—Slight.

FRUIT

General:
*Maturity when described.*—Eating-ripe.

*Date.*—May 10, 1994.
*Size.*—Slightly variable.
*Axial diameter.*—About 4.8 cm.
*Transverse in suture plane.*—About 4.6 cm.
*At right angles to suture plane.*—About 4.4 cm.
*Form.*—Symmetrical; oblong.
*Position of maximum diameter.*—Towards stem end.
*Symmetry about the suture.*—Asymmetric.
*Season ripening.*—Very early.
*Use.*—Market: fresh.
*Keeping quality.*—Good.
*Resistance to.*—Insects: Good, in Wasco, Calif. Diseases: Good, in Wasco, Calif.
*Shipping quality.*—Good.

Suture: Distinct.

Ventral surface:
*Shape.*—Rounded slightly.
*Lips.*—Equal.
*Depression of apex.*—Indistinct.
*Pistil base.*—Persisting.
*Pubescence at apex.*—Pubescent.
*Density of apex pubescence.*—Sparse.

Stem cavity:
*Shape.*—Flaring; circular; with suture showing on one side.
*Depth.*—About 0.6 cm.
*Breadth.*—About 1.1 cm.

Base:
*Shape.*—Rounded.

Apex:
*Shape.*—Rounded to truncate.

Pistil Point:
*Shape.*—Slightly depressed.

Stem:
*Length.*—About 0.4 cm; medium.
*Adherence to stone.*—Weak.

Skin:
*Thickness.*—Medium.
*Texture.*—Tender.
*Reticulation.*—Absent.
*Roughness.*—Absent.
*Tenacity.*—Tenacious to flesh.
*Tendency to crack.*—None in dry season.
*Color.*—Orange 24B.
*Over-Color (Blush).*—Red 45A.
*Down (pubescence).*—Scant.
*Bloom.*—Absent.

Flesh:
*Color.*—Orange 24A.
*Surface of the pit cavity.*—Orange 24A.
*Amygdalin.*—Wanting.
*Juice.*—Moderate.
*Sugar content.*—Medium to high.
*Texture.*—Medium.
*Fibers.*—Few; fine.
*Ripens.*—Even.
*Flavor.*—Vinous.
*Aroma.*—Distinct.
*Eating quality.*—Good.
*Ratio of stone to flesh.*—About 2.8:50 grams.

STONE

General:
*Adherence to flesh.*—Free.
*Fibers.*—Long; retains short fibers; like threads along ridges.
*Sizes.*—Small.
*Length.*—About 2.6 cm.
*Breadth.*—About 2.1 cm.
*Width of stalk end.*—About 0.3 cm.
*Angle of stalk end.*—Right angle.
*Thickness.*—About 1.1 cm.
*Form (profile).*—Elliptical; cuneate; toward the base.
*Form (ventral view).*—Sub-globular.
*Base.*—Nearly straight.
*Hilum.*—Narrow; oblong.
*Apex.*—Rounded.
*Position of maximum breadth.*—Towards middle.
*Sides.*—Equal.
*Surface.*—Central edge; ridged.
*Outgrowing keel.*—Partly developed.
*Ridges.*—Jagged; towards base.
*Ventrical edge.*—Thin.
*Dorsal edge.*—Medium.
*Color of dry stone.*—Greyed-Orange 164B.
*Tendency to split.*—None in dry season.

We claim:

1. A new and distinct variety of apricot tree cv. 'Suaprisix' as herein illustrated and described.

* * * * *